(12) United States Patent
Gilat

(10) Patent No.: US 6,589,946 B2
(45) Date of Patent: *Jul. 8, 2003

(54) BILE SALT CONJUGATES

(75) Inventor: Tuvia Gilat, Tel Aviv (IL)

(73) Assignee: Galmed International Limited, B'Kara (MT)

( * ) Notice: Subject to any disclaimer, the term of this patent is extended or adjusted under 35 U.S.C. 154(b) by 0 days.

This patent is subject to a terminal disclaimer.

(21) Appl. No.: 10/078,671

(22) Filed: Feb. 21, 2002

(65) Prior Publication Data

US 2002/0091111 A1 Jul. 11, 2002

Related U.S. Application Data

(63) Continuation of application No. 09/693,928, filed on Oct. 23, 2000, now Pat. No. 6,384,024, which is a continuation of application No. 09/675,656, filed on Sep. 29, 2000, now Pat. No. 6,395,722, which is a continuation of application No. PCT/IL99/00173, filed on Mar. 25, 1999.

(30) Foreign Application Priority Data

Apr. 8, 1998 (IL) ................................................ 123998

(51) Int. Cl.⁷ ............................. A61K 31/56; C07J 9/00; C07J 1/00
(52) U.S. Cl. ....................... 514/182; 552/549; 552/550; 552/551
(58) Field of Search .......................... 514/182; 552/549, 552/550, 557

(56) References Cited

U.S. PATENT DOCUMENTS

| | | | | |
|---|---|---|---|---|
| 4,439,366 A | * | 3/1984 | Scolastico et al. | 260/397.1 |
| 4,440,688 A | * | 4/1984 | Scolastico et al. | 260/397.1 |
| 6,384,024 B1 | * | 5/2002 | Gilat | 514/182 |

FOREIGN PATENT DOCUMENTS

DE 198 24 123 A1 * 5/1998

* cited by examiner

*Primary Examiner*—Barbara P. Badio
(74) *Attorney, Agent, or Firm*—Jacobson Holman PLLC (57) ABSTRACT

The present invention relates to bile acid or bile salt fatty acid conjugates (hereinafter called "BAFAC), to their use in dissolving cholesterol gallstones in bile, preventing their occurrence or recurrence, to their use in reducing or preventing arteriosclerosis and to methods for the treatment of said diseases. The conjugates are of the formula W—X—G in which G is a bile acid or bile salt radical, W stands for one or two saturated fatty acid radicals and X is either a direct bond or a bonding member between bile acid or bile salt and the fatty acid(s). The conjugation is advantageously performed at a position selected among the 3, 6, 7, 12 and 24 positions of the bile acid or bile salt nucleus. The fatty acids are preferably saturated fatty acids having 6–26 carbon atoms.

17 Claims, 10 Drawing Sheets

FIG. 4A
PaIC pure     in bile

FIG. 4B
Hamster bile control     PaIC fed

FIG. 5A

| | |
|---|---|
| 2 | n=20 |
| 4 | n=18 |
| 6 | n=16 |
| 8 | n=14 |
| 10 | n=12 |
| 12 | n=10 |
| 14 | n=4 |

| | |
|---|---|
| 3 | n=20 |
| 5 | n=18 |
| 7 | n=16 |
| 9 | n=14 |
| 11 | n=12 |
| 13 | n=10 |
| 15 | n=4 |

BILE SALT CONJUGATES

This is a continuing application of Ser. No. 09/693,928 filed Oct. 23, 2000, now U.S. Pat. No. 6,384,024, which in turn is a continuing application of Ser. No. 09/675,656, filed Sep. 29, 2000, now U.S. Pat. No. 6,395,722 which is a continuing application of PCT Application Ser. No. PCTIL99/00173, filed Mar. 25,1999.

FIELD OF THE INVENTION

The present invention relates to bile acid or bile salt fatty acid conjugates (hereinafter called "BAFAC"), to their use in dissolving cholesterol gallstones in bile, preventing their occurrence of recurrence, to their use in reducing or preventing arteriosclerosis and to methods for the treatment of said diseases.

BACKGROUND

It should be noticed that the terms bile acids and bile salts are similar and are used interchangeably.

Gallstones are found in about 15% of people in most industrialized countries. Most gallstones are cholesterol gallstones, i.e. cholesterol being their main component. Thus, cholesterol gallstones represent a major health problem. Bile is often supersaturated with cholesterol which tends to crystallize. The prevention of cholesterol crystallization in bile will prevent the formation of cholesterol gallstones or their recurrence after procedures such as lithotripsy, dissolution, or stone extraction. The residence time of newly secreted bile in the gallbladder is short—less than 12–24 hours. The prevention of cholesterol crystallization in bile during such a period could prevent gallstone formation.

It has been proven that cholesterol gallstones can be dissolved medically and their recurrence prevented using certain bile salts such as chenodeoxycholic or ursodeoxycholic acid. Bile salt therapy is, however, of low efficacy, is very time consuming and has been largely abandoned. More effective therapies are thus required.

Recent work has demonstrated the major role played by phospholipids in cholesterol solubilization in bile. (T. Gilat et al., Biochimica et Biophysica Acta, 1286, (1996), 95–115; Y. Ringel et al., Biochimica et Biophysica Acta, 1390, (1998), 293–300; and J. Hepatology, 28, (1998), 1008–1014.) Phospholipids are a major or sole component of cholesterol solubilizing lipid aggregates in bile. It has been demonstrated that the stepwise addition of phospholipids to bile will progressively prolong the nucleation time of the cholesterol in bile. (Z. Halpern et al., Gut, 34 (1993) 110–115).

Major differences between certain phospholipid molecular species in their cholesterol crystallization inhibiting potency in human or model biles have been demonstrated. Phospholipids differ from one another mainly in the fatty acids present in the stereospecific number sn-1 and/or sn-2 positions and in their head groups. It has been demonstrated that major prolongations in the nucleation time and major reductions in the cholesterol crystal growth rate and in the total cholesterol crystal mass are achieved with changes in phospholipid molecular species without changing the absolute or relative amounts of phospholips. Cholesterol crystallization was markedly delayed when the sn-2 fatty acid was saturated, when the head group was serine instead of choline, etc. (Y. Ringel et al., above).

It has also been shown that various phospholipid components by themselves (without the whole phospholipid molecule), e.g. saturated fatty acids such as palmitic acid or stearic acid; or phosphatidyl glycerol have strong cholesterol crystallization inhibiting activity.

Thus, enriching human bile with phospholipids in general, or specific phospholipids or their components, such as fatty acids would markedly retard cholesterol crystallization in bile and achieve the desired result.

The problem was how to enrich human bile in vivo with phospholipids or their components. When bile salts are fed to humans they are very efficiently absorbed, taken up by the liver and excreted into bile. This also applies to synthetic bile salt analogues. There are specific and very efficient transport mechanisms in the body for these purposes. Thus, when ursodeoxycholic acid (which is normally present in human bile in minute amounts) is fed regularly, it is absorbed and secreted into bile and eventually constitutes 30–50% of biliary bile acids. However, as indicated above, bile salt therapy for the dissolution of cholesterol gallstones is not satisfactory.

Phospholipids and their components are well absorbed and taken up by the liver. Phospholipid secretion into bile is, however, tightly regulated by the liver and only limited amounts and species of phospholipids are secreted into bile in association with the secretion of bile salts and cholesterol. There is at present no efficient method to modulate, quantitatively or qualitatively, human biliary phospholipid compositions to any considerable degree. When dietary phospholipids reach the liver, they may be metabolized, secreted into the blood or stored in the liver. Only small amounts and predetermined species are secreted into bile with minimal possibilities for modulation.

It has therefore been desirable to find a satisfactory method for the transport of phospholipids or one of their components into bile which would improve the solubilization of biliary cholesterol and prevent the formation of cholesterol gallstones or dissolve existing gallstones.

From Israel Patent Specification No. 95668 and corresponding U.S. Specifications there are known bile acid derivatives of general formula I:

in which G is a bile acid radical, W is an active compound moiety of a medicament and X is either a direct bond or a bonding member between said bile acid radical and the active compound. In said specifications a long list of substituents is given but it does not mention specifically W as standing for a fatty acid radical, neither for a saturated one nor for an unsaturated one, i.e. said specifications do not mention anything about BAFAC.

Moreover, among all the objects of said compounds there cannot be found even a hint that any of said compounds may be utilized to enhance the solubilization of biliary cholesterol, to prevent the formation of cholesterol gallstones, to dissolve existing cholesterol gallstones, to reduce or prevent arteriosclerosis.

SUMMARY OF THE INVENTION

It has now been found that bile acids or salts conjugated with fatty acids (saturated or unsaturated) either directly or via a connecting bond X (both possibilities are covered by the term BAFAC) can serve as vehicles to transport the fatty acids into the bile using the very efficient entero-hepatic circulation of bile acids and salts. It has also been shown that BAFAC are absorbed from the intestine, taken up by the liver and secreted into bile. Said BAFAC improved cholesterol solubilization in bile and markedly retarded its crystallization. Said BAFAC are therefore useful agents for the prevention of the formation or recurrence of cholesterol gallstones and for the dissolution of cholesterol gallstones.

The administration of BAFAC has also an inhibiting effect on cholesterol crystallization in the vascular tree. In the physiologic situation ingested bile acids or salts are absorbed in the intestine, transported via the portal vein to the liver and excreted via the bile into the intestine. They thus recirculate in the entero-hepatic circulation, with only minute amounts reaching the systemic circulation (the vascular tree). The BAFAC behave more like lipids, which after intestinal absorption are transported via the lymph to the systemic circulation. The BAFAC were shown to be transported both via the lymph and via the portal vein. By both routes they are taken up by the liver and secreted into the bile. At each entero-hepatic circulation they are excreted into the intestine, are again partly reabsorbed via the lymph and recirculated into the vascular tree prior to liver uptake. As there are daily 10–12 cycles of entero-hepatic circulation, the net effect will be recirculation of the BAFAC in the vascular tree.

Administration of BAFAC orally in divided doses in the course of the day will enhance this effect. The inhibiting effect of BAFAC on cholesterol crystallization has been proven. Thus, also their value in reducing and/or preventing cholesterol crystallization in the vascular tree, i.e. in arteriosclerosis.

The present invention thus consists in bile acid or bile salt fatty acid conjugates of general formula II:

W—X—G in which G and X have the same meaning as in formula I and W stands for one or two fatty acid radicals.

As suitable bile acids there may be mentioned, e.g., cholic acid, chenodeoxycholic acid, ursodeoxycholic acid, deoxycholic acid and derivatives and analogues thereof, etc. The bile acids utilized may be unconjugated or, as in bile, be conjugated with glycine, taurine or a suitable amino acid. These possibilities are within the definition of a bile acid and thus within the scope of the present invention. The conjugation with the fatty acid radical is mostly performed at position 3 of the nucleus depending on the bile acid being used. It is also possible to perform the conjugation with the fatty acid radical at different positions, e.g. 6, 7, 12 and 24. When the bile acid is conjugated with glycine or taurine the conjugation with the fatty acid radical cannot be performed in position 24. The conjugation between the fatty acid radical and the bile acid can be in the α or the β configuration.

The bonding member X is advantageously an —NH— group or an —O— group or a direct bond.

Preferred fatty acids are saturated ones which have suitably 6–26 carbon atoms, advantageously those having 14 to 22 carbon atoms. Preferred saturated fatty acids are behenylic acid, arachidylic acid, stearic acid, palmitic acid and myristylic acid.

When W stands for two fatty acids they are suitably conjugated at positions 3 and 7.

The present invention also consists in a pharmaceutical composition enabling the dissolution of cholesterol gallstones in bile and preventing the formation thereof; and enabling the prevention and/or reduction of arteriosclerosis, comprising as active ingredient a bile acid fatty acid derivative of general formula II.

Said composition may have the form of a tablet, a capsule, a solution, an emulsion, etc.

Said composition may comprise additional compounds such as carriers, solvents, emulgators, enhancers of absorption, inhibitors of cholesterol synthesis or secretion into the bile, etc. Said composition should advantageously comprise 0.1–1.5 g of the active ingredient.

The composition is suitably ingested once daily, preferably at bedtime. It may also be ingested in divided doses during the day.

The present invention also consists in the use of a bile acid fatty acid derivative of general formula II or of a pharmaceutical composition comprising same for the dissolution of cholesterol gallstones in bile and for the prevention of the formation thereof.

The present invention also consists in the use of a bile acid fatty acid derivative of general formula II or of a pharmaceutical composition comprising same for the prevention and/or reduction of arteriosclerosis.

The present invention also consists in a method for the dissolution of cholesterol gallstones in bile and for the prevention of the formation thereof by administering a bile acid fatty acid derivative of general formula II or a pharmaceutical composition comprising same.

The present invention also consists in a method for the prevention and/or reduction of arteriosclerosis by administering a bile acid fatty acid derivative of general formula II or a pharmaceutical composition comprising same.

The present invention will now be illustrated with reference to the accompanying Examples and drawings without being limited by them.

BRIEF DESCRIPTION OF THE DRAWINGS

In said drawings.

A—Control solution. B, C—Replacement of 10% and 20% of Na taurocholate (NaTC) by equimolar amounts of PalC, respectively. D—Replacement of 20% of pospholids by PalC. E, F—addition of 10 mM and 20 mM PalC to the solution, respectively.

DETAILS

EXAMPLE I

Figure 5A:
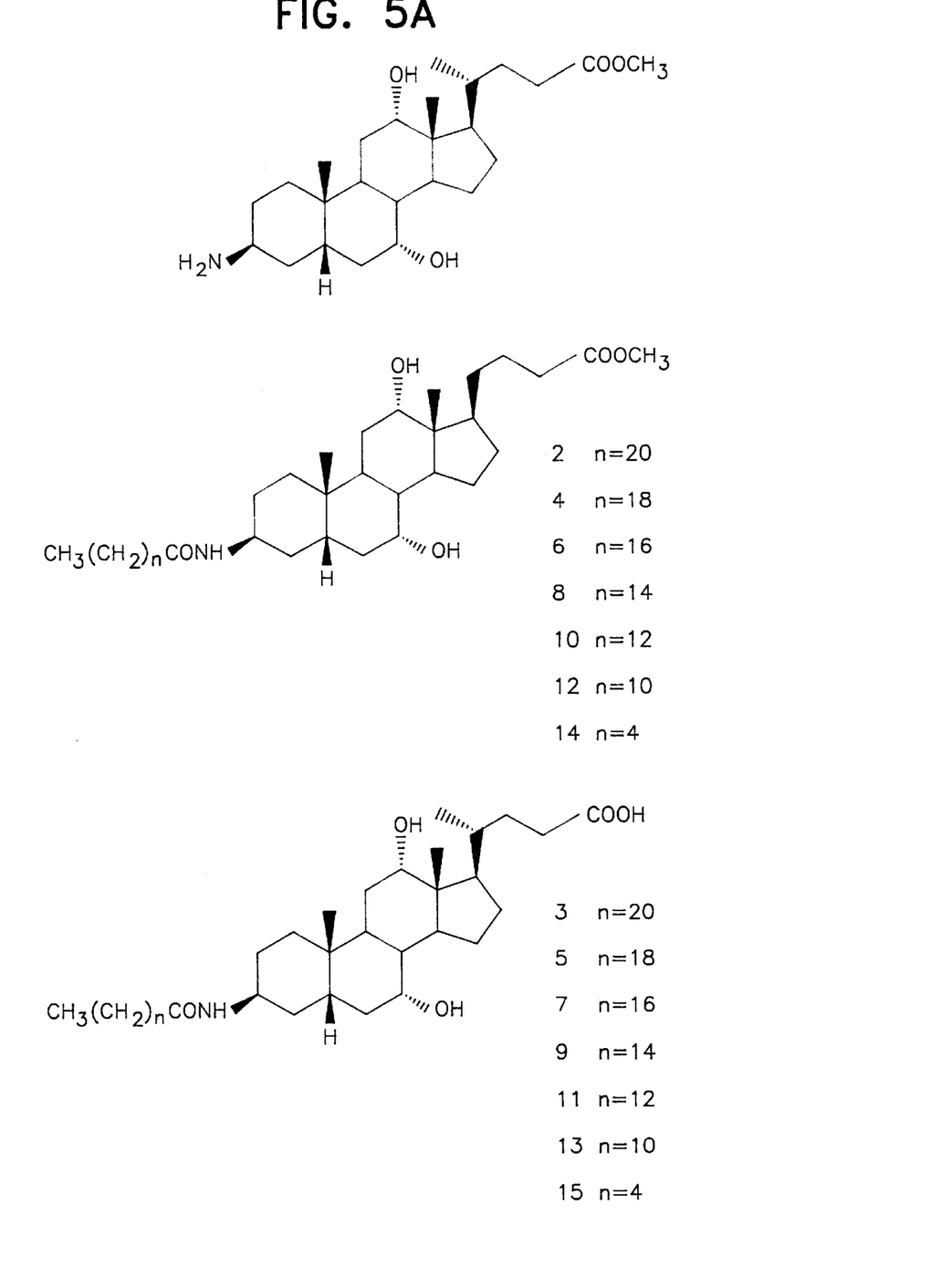
FIG. 5A shows steps in the conjugation of cholic acid (at C-3) with: behenylic acid (C-22), arachidic acid (C-20), stearic acid (C-18), palmitic acid (C-16), myristic acid (C-14), lauric acid (C-12) and caproic acid (C-6)
Figure 5B:
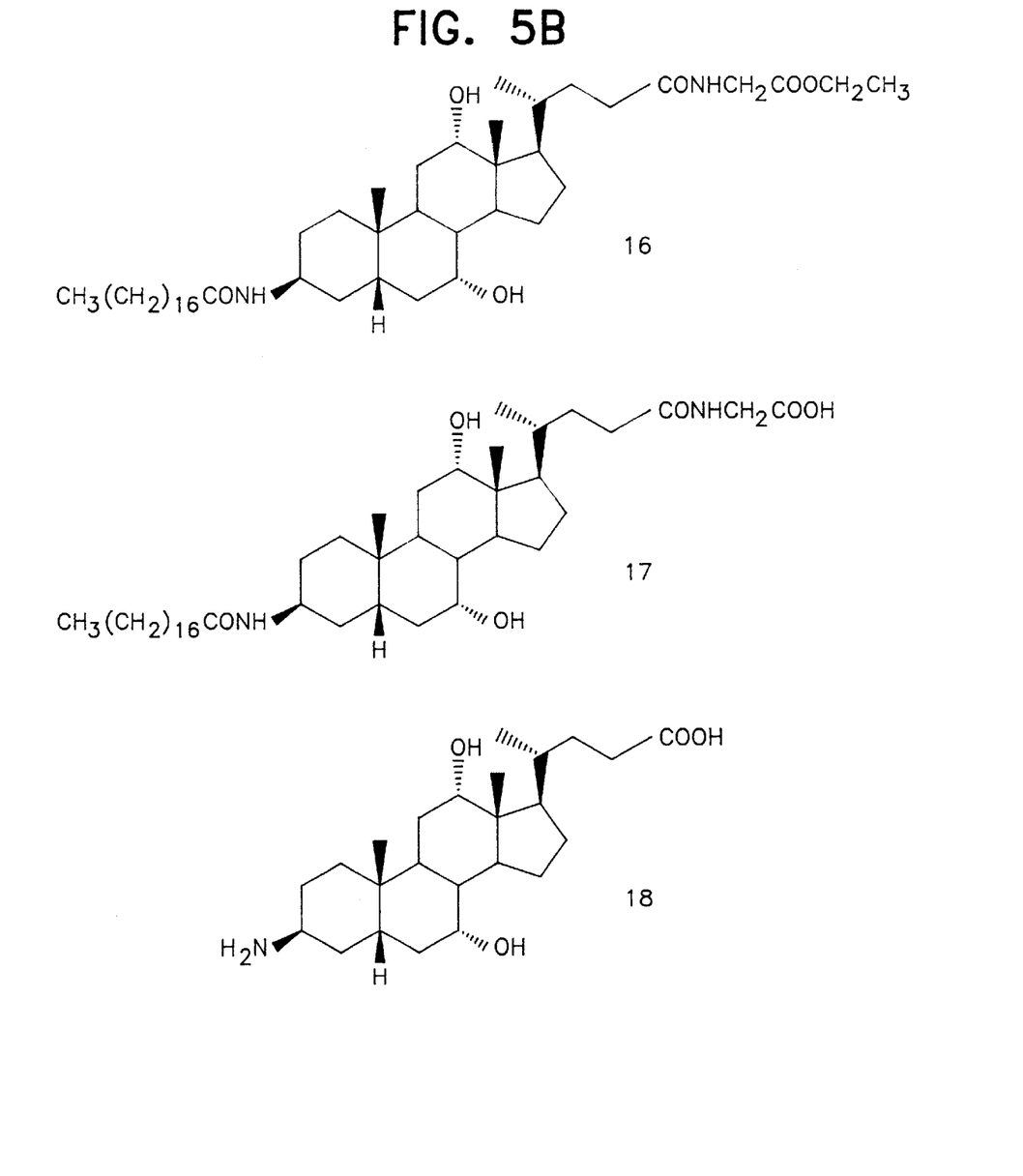
FIG. 5B shows stages in the synthesis of glycine conjugated stearoyl-cholate.
Figure 5C:
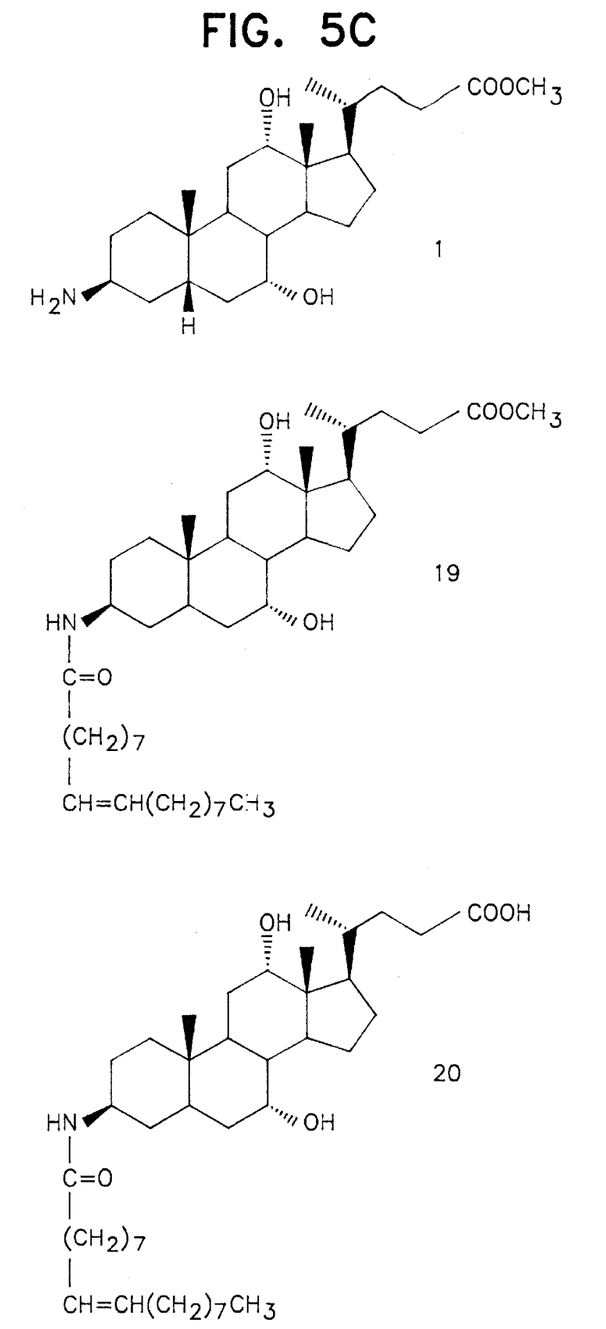
FIG. 5C shows conjugation of oleoyl-cholate.
Figure 5D:
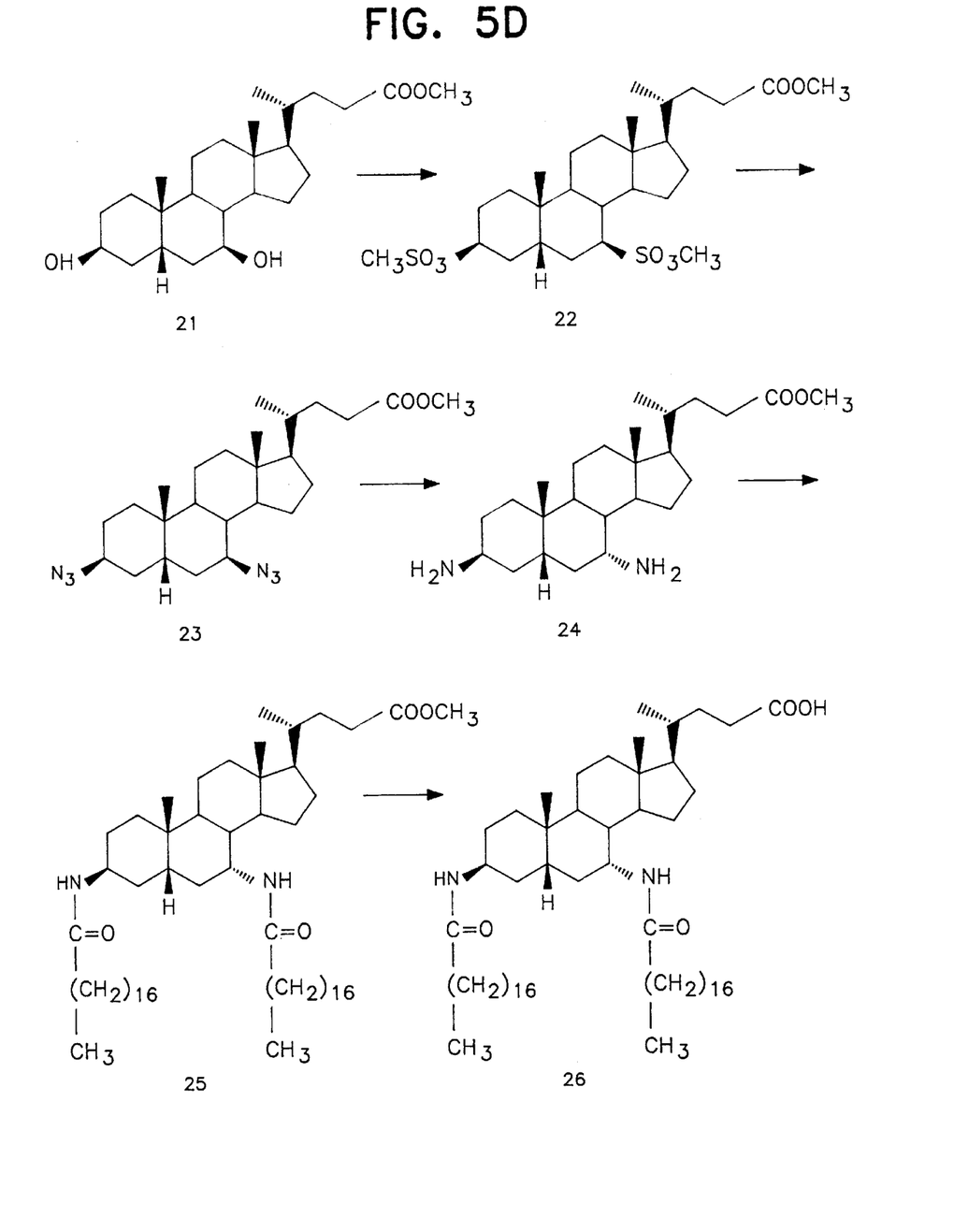
FIG. 5D shows conjugation of cholic acid with two molecules of stearic acid at positions C-3 and C-7 of the bile acid nucleus.

3β-Behenylamido-7α,12α-dihydroxy-5β-cholan-24-oic Acid (FIG. 5A-3)

(a) 1.15 g of 3β-amino-7α,12α-dihydroxy-5β-cholan-24-oic methylester (FIG. 5A-1) [Fr Patent 1017756 Dec. 18 1952, Chem. Abstr. 52:1293c] were dissolved in 30 ml dry dimethyl formamide and treated with 15 ml triethyl amine under stirring. 1.13 g of behenoyl chloride in 10 ml dimethyl formamide were added dropwise to the resulting solution, and the stirring was continued overnight. The reaction mixture was poured into water extracted with methylene chloride, the organic fraction was then dried over sodium sulfate, evaporated to dryness and chromatographed over silica gel with a mixture of ethyl acetate and hexane (6:4 and 8:2), to give 0.8 g of 3β-behenylamido-7α,12α-dihydroxy-5β-cholan-24-oic of the methyl ester (FIG. 5A-2).

$^1$H-NMR (CDCl$_3$) δ, ppm: 0.69 (s, CH$_3$-18), 0.88 (t, J=1 Hz, CH$_3$-23), 0.95 (s. CH$_3$-19), 0.99 (d, J=3 Hz, CH$_3$-21), 1.25, 1.14 [(s, CH$_2$)$_{20}$], 2.14 (t, J=5 Hz, CH$_3$-behenyl), 3.67 (s-COOCH$_3$), 3.91 (d, J=1.5 Hz, CH-7), 3.96 (s, J=4 Hz, CH-12), 3.99 (m, CH-3), 5.60 (d, J=4.5 Hz, —CH$_2$CO—).

(b) The above methyl ester, 0.45 g, was dissolved in 20 ml methanol, treated with 2 ml 1N sodium hydroxide and left for 24 h at room temperature. The methanol was then distilled off, 10 ml water were added and the reaction mixture was extracted with ethyl acetate. The water fraction was then acidified with diluted acid chloride, resulting in a white precipitate which was washed with water, to give 0.41 g of the pure 3β-behenylamido-7α,12α-dihydroxy-5β-cholan-24-oic acid (FIG. 5A-3).

EXAMPLE II

3β-Arachidylamido-7α,12α-dihydroxy-5β-cholan-24-oic Acid (FIG. 5A-5)

(a) 1.0 g of 3β-amino-7α,12α-dihydroxy-5β-cholan-24-oic methylester (FIG. 5A-1) [see Example I] was dissolved in 30 ml dry dimethylformamide and treated with 15 ml triethyl amine under stirring. 1.0 g of arachidoyl chloride in 10 ml dimethylformamide was added dropwise to the resulting solution, and the stirring was continued overnight. The reaction mixture was poured into water, extracted with methylene chloride, the organic fraction was then dried over sodium sulfate, evaporated to dryness and chromatographed over silica gel with a mixture of ethyl acetate and hexane (6:4 and 8:2), to give 0.6 g 3β-arachidylamido-7α,12α-dihydroxy-5β-cholan-24-oic methylester (FIG. 5A-4).

$^1$H-NMR (CDCl$_3$) δ, ppm: 0.70 (s, CH$_3$-18), 0.88 (t, J=6 Hz, CH$_3$-23), 0.95 (s, CH$_3$-19), 0.99 (d, J=3. Hz, CH$_3$-21) 1.25, 1.14 [(s, CH$_2$)$_{18}$], 2.14 (t, J=5 Hz, CH$_3$-arachidyl), 3.67 (s-COOCH$_3$), 3.91 (d, J=1.5 Hz, CH-7), 3.96 (t, J=4 Hz, CH-12), 4.4 (m, CH-3), 5.60 (d, J=4.5 Hz, —CH$_2$CONH).

(b) 0.5 g 3β-arachidylamido-7α,12α-dihydroxy-5β-cholan-24-oic methylester (FIG. 5A-4) were dissolved in 20 ml methanol, treated with 2 ml 1N sodium hydroxide and left for 24 h at room temperature. The methanol was then distilled off, 10 ml water were added and the reaction mixture was extracted with ethyl acetate. The water fraction was then acidified with diluted hydrogen chloride, resulting in a white precipitate which was washed with water, to give 0.7 g of the pure 3β-arachidylamido-7α,12α-dihydroxy-5β-cholan-24-oic acid (FIG. 5A-5).

EXAMPLE III

3β-Stearylamido-7α,12α-dihydroxy-5β-cholan-24-oic Acid (FIG. 5A-7)

Method 1

(a) 1.15 g 3β-amino-7α,12α-dihydroxy-5β-cholan-24-oic methylester (FIG. 5A-1) [see Example I] were dissolved in 30 ml dry dimethylformamide and treated with 15 ml triethyl amine under stirring. 1.13 g of stearoyl chloride in 10 ml dimethyl formamide were added dropwise to the resulting solution, and the stirring was continued overnight. The reaction mixture was poured into water extracted with methylene chloride; the organic fraction was then dried over sodium sulfate, evaporated to dryness and chromatographed over silica gel with a mixture of ethyl acetate and hexane (6:4 and 8:2), to give 0.68 g 3β-stearylamido-7α,12α-dihydroxy-5β-cholan-24 oic methylester (FIG. 5A-6).

$^1$H-NMR (CDCl$_3$) δ, ppm: 0.69 (s, CH$_3$-18), 0.88 (t, J=1 Hz, CH$_3$-23), 0.95 (s, CH$_3$-19), 0.99 (t, J=3. Hz, CH$_3$-21), 1.25, 1.14 [(s, CH$_2$)$_{16}$]2.14 (t, J=5 Hz, CH$_3$-stearyl), 3.67 (s-COOCH$_3$), 3.91 (d, J=1.5 Hz, CH-7), 3.99(m, CH-3), 4.4 (m, CH-3), 5.60 (d, J=4.5 Hz, —CH$_2$CONH).

(b) 0.45 g 3β-stearylamido-7α,12α-dihydroxy-5β-cholan-24-oic methylester (FIG. 5A-6) were dissolved in 20 ml methanol, treated with 2 ml 1N sodium hydroxide and left for 24 h at room temperature. The methanol was then distilled off, 10 ml water were added and the reaction mixture was extracted with ethyl acetate. The water fraction was then acidified with diluted hydrogen chloride, resulting in a white precipitate which was washed with water, to give 0.41 g of the 3β-stearylamido 7α,12α-dihydroxy-5β-cholan-24-oic acid (FIG. 5A-7). mp 63–65° C.

Method 2

2.5 g 3β-amino-7α,12α-dihydroxy-5β-cholanoic-24-oic acid (prepared according to Kramer et al., J. of Lipid Research 24, 910, 1983) were dissolved in acetonitrile and added to a stirred solution of 1.2 g stearic acid and 3.6 g N-hydroxy succinamide in the same solvent. After 8 h the precipitate was filtered, washed with the solvent and evaporated to dryness. The residue was added to a solution of 1.2 g of stearic acid in 10 ml N-methyl morpholine and N,N'-dimethyl formamide (1:3). After being kept at room temperature overnight, the solution was diluted with water, extracted with ethyl acetate, to give 0.6 g of the acid (FIG. 5A-7), identical to that of Method 1.

Method 3

A solution of 6 g stearoyl chloride was added dropwise to a stirred solution of 1.6 g of the amine (FIG. 5B-18) in toluene at 0°, and left at the same temperature for 1 h. The resulting solution was heated at 50° for another hour, acidified with 3N-hydrochloride acid, and then filtered. The solid material was washed with water and dried at 45°, to give the acid (FIG. 5A-7), identical with that described above.

EXAMPLE IV

3β-Palmitylamido-7α,12α-dihydroxy-5β-cholan-24-oic Acid (FIG. 5A-9)

Method 1

(a) 1.0 g of the 3β-amino-7α,12α-dihydroxy-5β-cholan-24-oic methylester (FIG. 5A-1) [See Example I] was dissolved in 30 ml dry dimethyl formamide and treated with 15 ml triethyl amine under stirring. 0.8 g of palmitoyl chloride in 10 ml dimethyl formamide was added dropwise to the resulting solution, and the stirring was continued overnight. The reaction mixture was poured into water extracted with methylene chloride, the organic fraction was then dried over sodium sulfate, evaporated to dryness and chromatographed over silica gel with a mixture of ethyl acetate and hexane (6:4 and 8:2), to give 0.5 g 3β-palmitylamido-7α,12α-dihydroxy-5β-cholan-24-oic methylester (FIG. 5A-8)

$^1$H-NMR (CDCl$_3$) δ, ppm: 0.66 (s, CH$_3$-11), 0.88 (t, J=1 Hz, CH$_3$-23), 0.91 (s, CH$_3$-19), 0.96 (d, J=3.5 Hz, CH$_3$-21), 1.22, 1.14 [(s, CH$_2$)$_{14}$], 2.13 (t, J=5 Hz, CH$_3$-palmityl), 3.67 (s-COOCH$_3$), 3.82 (d, J=1.5 Hz-CH$_7$), 3.96 (s, J=3.9 Hz, CH-12), 4.09 (m, CH-3), 5.63 (d, J=4.5 Hz, —CH$_2$CONH).

(b) The above methyl ester, 0.45 g, was dissolved in 20 ml methanol, treated with 2 ml 1N sodium hydroxide and left for 24 h at room temperature. The methanol was then distilled off, 10 ml water were added and the reaction mixture was extracted with ethyl acetate. The water fraction was then acidified with diluted hydrogen chloride, resulting in a white precipitate which was washed with water, to give 0.4 g of the pure 3β-palmitylamido-7α,12α-dihydroxy-5β-cholan-24-oic acid (FIG. 5A-9).

Method 2

2.5 g 3β-amino-7α,12α-dihydroxy-5β-cholanoic-24-oic acid (FIG. 5B-18) (prepared according to Kramer et al., J. of Lipid Research, 24, 910, 1983) were dissolved in acetonitrile and added to a stirred solution of 1.2 g palmitic acid and 3.6 g N-hydroxy succinamide in the same solvent. After 8 h the precipitate was filtered, washed with the solvent and evaporated to dryness. The residue was added to a solution of 1.2 g of palmitic acid in 10 ml N-methyl morpholine and N,N'-dimethylformamide (1:3). After being kept at room temperature overnight, the solution was diluted with water, extracted with ethyl acetate, to give 0.6 g of the acid (FIG. 5A-9), identical to that of Method 1.

EXAMPLE V

3β-Myristylamido-7α,12α-dihydroxy-5β-cholan-24-oic Acid (FIG. 5A-11)

(a) 0.5 g of 3β-amino-7α,12α-dihydroxy-5β-cholan-oic methylester (1) [See Example I] were dissolved in 30 ml dry dimethylformamide and treated with 15 ml triethyl amine under stirring. 0.4 g myristoyl chloride in 10 ml dimethylformamide were added dropwise to the resulting solution, and the stirring was continued overnight. The reaction mixture was poured into water, extracted with methylene chloride, the organic fraction was then dried over sodium sulfate, evaporated to dryness and chromatographed over silica gel with a mixture of ethyl acetate and hexane (6:4 and 8:2), to give 0.4 g 3β-myristylamido-7α,12α-dihydroxy-5β-cholan-24oic methylester (FIG. 5A-10).

$^1$H-NMR (CDCl$_3$) δ, ppm: 0.69 (s, CH$_3$-18), 0.88 (t, J=1 Hz, CH$_3$-23), 0.95 (s, CH$_3$-19), 0.99 (d, J=3. Hz, CH$_3$-21), 1.25 [(s, CH$_2$)$_{12}$], 2.14 (t, J=5 Hz, CH$_3$-myristyl), 3.67 (s-COOCH$_3$), 3.91 (d, J=1.5 Hz —CH-7), 3.99 (d, J=4 Hz, CH-12), 4.4 (m, CH-3), 5.60 (d, J=4.5 Hz, —CH$_2$CONH).

(b) 0.45 g 3β-myristylamide-7α,12α-dihydroxy-5β-cholan-24-oic methylester (FIG. 5A-10) was dissolved in 20 ml methanol, treated with 2 ml 1N sodium hydroxide and left for 24 h at room temperature. The methanol was then distilled off, 10 ml water were added and the reaction mixture was extracted with ethyl acetate. The water fraction was then acidified with diluted hydrogen chloride, resulting in a white precipitate which was washed with water, to give 0.26 g of pure acid (FIG. 5A-11).

EXAMPLE VI

3β-Laurylamido-7α,12α-dihydroxy-5β-cholan-24-oic Acid (FIG. 5A-13)

(a) 0.6 g of 3β-amino-7α,12α-dihydroxy-5β-cholan-24-oic methylester (FIG. 5A-1) were dissolved in 30 ml dry dimethyl formamide and treated with 15 ml triethyl amine under stirring. 0.6 g of lauryl chloride in 10 ml dimethyl formamide was added dropwise to the resulting solution, and the stirring was continued overnight. The reaction mixture was poured into water extracted with methylene chloride, the organic fraction was then dried over sodium sulfate, evaporated to dryness and chromatographed over silica gel with a mixture of ethyl acetate and hexane (6:4 and 8:2), to give 0.5 g 3β-laurylamido-7α,12αdihydroxy-5β-cholan-24-oic methylester (FIG. 5A-12).

$^1$H-NMR (CDCl$_3$) δ, ppm: 0.67 (s, CH$_3$-18), 0.89 (t, J=1 Hz, CH$_3$-23), 0.94 (s, CH$_3$-19), 0.99 (d, J=3. Hz, CH$_3$-21), 1.25 [(s, CH$_2$)$_{10}$], 2.14 (t, J=5 Hz, CH$_3$-lauryl), 3.67 (s-COOCH$_3$), 3.91 (d, J=1.5 Hz, CH-7), 3.99 (t, J=3.95 Hz, CH-12), 4.4 (m, CH-3), 5.60 (d, J=4.5 Hz, —CH$_2$CONH).

(b) 0.45 g 3β-laurylamido-7α,12α-dihydroxy-5β-cholan-24-oic methylester (FIG. 5A-12) was dissolved in 20 ml methanol, treated with 2 ml 1N sodium hydroxide and left for 24 h at room temperature. The methanol was then distilled off, 10 ml water were added and the reaction mixture was extracted with ethyl acetate. The water fraction was then acidified with diluted hydrogen chloride, resulting in a white precipitate which was washed with water, to give 0.41 g of the pure acid (FIG. 5A-13), mp. 82–88.

Example VII

3β-Caprylamido-7α,12α-dihydroxy-5β-cholan-24-oic Acid (FIG. 5A-15)

(a) 1.0 g of 3β-amino-7α,12α-dihydroxy-5β-cholan-24-oic Acid (FIG. 5A-15) methylester (FIG. 5A-1) [see Example I] was dissolved in 30 ml dry methylene chloride and treated with 15 ml triethyl amine under stirring. 1.2 g of caproyl chloride acid in 10 ml methylene chloride were added dropwise to the resulting solution, and the stirring was continued overnight. The reaction mixture was poured into water extracted with methylene chloride, the organic fraction was then dried over sodium sulfate, evaporated to dryness and chromatographed over silica gel with a mixture of ehtyl acetate and hexane (6:4 and 8:2), to give 0.7 g 3β-caprylamido-7α,12α-dihydroxy-5β-cholan-24-oic methylester (FIG. 5A-14)

$^1$H-NMR (CDCl$_3$) δ, ppm: 0.69 (s, CH$_3$-18), 0.88 (t, J=1 Hz, CH$_3$-23), 0.95 (s, CH$_3$-19), 0.99 (t, J=3. Hz, CH$_3$-21), 1.25 [(s, CH$_2$)$_4$], 2.14 (t, J=5 Hz, CH$_3$-capryl), 3.67 (s-COOCH$_3$), 3.91 (d, J=1.5 Hz, CH-7), 3.99 (t, J=4 HzCH-12), 4.4 (m, CH-3), 5.60 (d, J=4.5 Hz —CH$_2$CONH).

(b) 0.5 g 3μ-caprylamido-7α,12α-dihydroxy-5μ-cholan-24-oic methylester (FIG. 5A-14) were dissolved in 20 ml methanol, treated with 2 ml 1 N sodium hydroxide and left for 24 h at room temperature. The methanol was then distilled off, 10 ml water were added and the reaction mixture was extracted with ethyl acetate. The water fraction was then acidified with diluted hydrogen chloride, resulting in a white precipitate which was washed with water, to give 0.4 g of pure acid (FIG. 5A-15).

EXAMPLE VIII

N-(-Carboxymethyl)-3β-stearylamido-7α,12α-dihydroxy-5β-cholane-24 Amide (FIG. 5B-17

(a) 0.5 g 3β-stearylamido-7α,12α-dihydroxy-5β-cholanoic acid (FIG. 5A-7) was dissolved in 25 ml dry 1,4-dioxane and was cooled to −10°. The stirred solution was treated with 0.5 ml triethylamine, then with 0.085 ml chloroethyl formate and stirred at the same temperature for 15 min. The solution was left to reach room temperature, treated with 0.1 ml triethylamine and with 14 g ethyl glycine hydrochloride, and left overnight. The reaction mixture was poured into water, extracted with ethyl acetate and washed with water. The extract was evaporated to dryness and chromatographed on silica gel, using a mixture of ethyl acetate:hexane 60:40, pure ethyl acetate and then ethyl acetate:methanol 9:1, to give 0.27 g of the product (FIG. 5B-16).

(b) 0.27 g of the above compound was dissolved in 20 ml methanol and treated with 2 ml sodium hydroxide 1N. After 24 h the methanol was evaporated till dryness, dissolved in water and extracted with ethyl acetate. The aqueous fraction was acidified with HCL 1N. The precipitate obtained was washed with water and dried, to give 0.24 g of the dry material (FIG. 5B-17).

EXAMPLE IX

3β-Oleylamido-7α,12α-dihydroxy-5β-cholan-24-oic Acid (FIG. 5C-20)

(a) 1.6 g 3β-amino-7α,12α-dihydroxy-5β-cholan-24-oic methylester (FIG. 5A-1) were dissolved in 30 ml dry dimethyl formamide and treated with 3 ml triethyl amine under stirring. A solution of 1.38 g oleyl chloride in 10 ml dry DMF was added dropwise, and the resulting solution was left at room temperature overnight. The reaction mixture was poured into water, extacted with ethyl acetate, the organic fraction was purified by washing with diluted hydrochloric acid, sodium bicarbonate and then with water. Evaporation to dryness in vacuum resulted in 3.1 g which were chromatographed over silica gel, using a mixture of ethyl acetate/hexane (4:6 and 10:8) to give 1.8 g of the methyl ester. (FIG. 5C-19).

(b) A solution of 1.2 g methyl ester in 20 ml methanol was treated at room temperature with a solution of 5 ml sodium hydroxide 1N and kept at room temperature for 48 hours and then evaporated to dryness. The residue was dissolved in 20 ml water and extracted with 25 ml ethyl acetate 3 times. The water extract was acidified with a hydrochloric solution to give a precipitate which was filtered. This residue was chromatographed on silica gel with a mixture of ethyl acetate:hexane:acetic acid (10:4:0.3), to give 0.3 g of 3β-oleylamido-7α,12α-dihydroxy-5β-cholan-24-oic acid (FIG. 5C-20).

EXAMPLE X

3β,7α-Distearylamido-5β-ursodeoxycholan-24-oic Acid (FIG. 5D-26)

(a) 20 g ursodesoxy-cholan-24-oic acid were dissolved in 200 ml abs. methanol, treated with 1 ml conc. sulfuric acid and stirred for 24 hrs. Most of the solvent was distilled off and the residue was poured into water and extracted with methylene chloride. The organic extract was washed with a solution of sodium bicarbonate and of sodium chloride, and evaporated to dryness resulting in 19.5 g of the 3α,7β-dihydroxy-5β-ursodeoxycholan-24-oic acid methyl ester. (FIG. 5D-21) $^1$H-NMR (CDCl$_3$) δ, ppm: 0.66 (s, CH$_3$-18), 0.90 (t, J=1 Hz, CH$_3$-23), 0.93 (s, CH$_3$-19), 0.94 (d, J=3 Hz, CH$_3$-21), 3.58 (m, CH-3, CH-7), 3.65 (s-COOCH$_3$)

(b) 4.06 g of the methyl ester (FIG. 5D-21) were dissolved in 30 ml dry pyridine and cooled to 0° C. The reaction mixture was stirred and treated dropwise for 15 min. with a solution of 1.49 g methane-sulfonyl chloride in 5 ml pyridine. After being left standing for 3 hrs. at the same temperature, the reaction mixture was poured on ice and water, and then extracted with ethyl acetate. The organic phase was washed with hydrochloric acid, sodium bicarbonate and sodium chloride solution, filtered and evaporated in vacuum. The residue consisting of 4 compounds was chromatographed over a silica column using as eluant a mixture of ethyl acetate and hexane. The less polar compound, 5.3 g, was the desired 3α,7β-dimesyl-5β-ursodeoxycholanoic acid 24-oic methyl ester. (FIG. 5D-22).

$^1$H-NMR (CDCl$_3$) δ, ppm: 0.65 (s, CH$_3$-18), 0.90 (d, J=4 Hz, CH$_3$-23), 0.97 (s, CH$_3$-19), 1.2 (t, J=3 Hz, CH$_3$-21), 2.97 (s, CH$_3$SO$_2$) 2.98 (s, CH$_3$SO$_2$), 3.64 (s, CH$_3$SO$_2$) 4.09 (q, J=12 Hz, H-7), 4.62 (m, H-7).

(c) 5.65 g of the dimesyl derivative were dissolved in 50 ml dry DMF, treated with dry sodium azide and heated to 130° for 2 hrs. The reaction mixture was cooled, poured into ice water and extracted with ethyl acetate. The extract was then washed with a solution of sodium acetate and sodium chloride, filtered and evaporated to dryness, resulting in 4.6 g of the 3β,7α-diazido-5β-ursodeoxycholan-24-oic acid methyl ester (FIG. 5D-23).

(d) 4.5 g of the diazido compound (FIG. 5D-23) were dissolved in 120 ml methanol to which 150 mg of 5% palladium on carbon were added and hydrogenated at atmospheric pressure for 4 days. The hydrogenation was repeated with additional 150 mg of 5% palladium on carbon. The hydrogenated mixture was filtered and evaporated in vacuum to give 3 g of the 3β,7α-diamino-5β-ursodeoxycholan-24-oic acid methyl ester (FIG. 5D-24).

$^1$H-NMR (CDCl$_3$) δ, ppm: 0.65 (s, CH$_3$-18), 0.92 (d, J=4 Hz, CH$_3$-23), 0.96 (s, CH$_3$-19), 1.2 (t, J=3 Hz, CH$_3$-21), 3.68 (s-COOCH$_3$), 3.72, 3.95(m, 2 H-7, 3).

(e) 1.47 g of the 3β,7α-diamino-5β-ursodeoxycholan-24-oic acid methyl ester (FIG. 5D-24) were dissolved in 50 ml of a dry 1:1 mixture of DMSO and DMF, treated with 2 ml triethylamine and 30 mg dimethylamino pyridine and 5.1 g stearic anhydride. The reaction mixture was heated to 50°, stirred for 18 hrs, poured into ice-water and extracted 3 times with ethyl acetate. The organic phase was washed with hydrochloric acid, sodium bicarbonate and sodium chloride solution. After evaporating the organic solvent, 2.05 g of an oily residue were obtained. Separation on silica gel using ethyl acetate:hexane as an eluant (1:4) resulted in a number of fractions, one of which, 80 mg, was the desired 3β,7α-distearylamido-5β-ursodeoxycholanoic acid-24-methylester (FIG. 5D-25), according to its MS and $^1$H-NMR MS FAB: MH+ 937 (MW) 936).

$^1$H-NMR (CDCl$_3$) δ, ppm: 0.66 (s, CH$_3$-18), 0.86 (d, J=4 Hz, CH$_3$-23), 0. 96 (s, CH$_3$-19), 1.2 (t, J=3 Hz, CH$_3$-21), 1.26 [s, (CH$_2$)$_{16}$], 3.64 (s, COOCH$_3$), 3.05 (d J=7. Hz, H-7) 5.75 (m, H-3).

(f) 78 mg of the methylester (FIG. 5D-25) were dissolved in 20 ml methanol, treated with 2 ml sodium hydroxide 1 N and left for 48 hrs at room temperature. The methanol was evaporated in vacuum, the residue was dissolved in 25 ml water, filtered and then acidified with diluted hydrochloric acid to give a precipitate which consisted of 3β,7α-distearylamido-5β-ursodeoxycholan-24-oic acid (FIG. 5D-26y).

EXAMPLE XI

Materials and Methods

Cholesterol (Sigma, St. Louis, Mo.) was twice recrystallized from hot ethanol; Na-taurocholate (Na-TC; Sigma, St. Louis, Mo.) was twice recrystallized from ethanol and ether (J. L Pope, J. Lipid Res. 8, (1967) 146–147); egg yolk lecithin (EYL) (Avanti Polar Lipids, Alabaster, Al.) was used without further purification. All lipids used in this study were pure by TLC standard. The synthetic bile acid conjugate used in Examples XII to XIV was palmitylamido-7α,12α-dihydroxy-5β-cholan-24-oic acid (PalC) (prepared as described in Example IV).

1. Preparation of Biles

A. Model Bile

EYL, cholesterol and Na-TC mixtures were dissolved in $CHCl_3/CH_3OH$ (2:1 v/v), dried under $N_2$ at room temperature, lyophilized overnight and kept at −20°C. under argon until used. Model bile solutions were prepared by suspending the dried lipids in 150 mM NaCl, 1.5 mM disodium EDTA, 50 mM Tris-HCl pH 8.0 and incubating the suspension at 55° C. for 1 hour. The solubilized model biles were incubated, in sealed vials under argon, at 37° C. for the duration of the experiment. Aliquots from the models were examined daily.

All models were prepared in triplicate and were kept at the same conditions throughout the experimental period.

The composition of the model bile was:

cholesterol 15 mM, EYL 30 mM, Na-TC 150 mM.

One hundred per cent EYL was used for preparation of the control solution. The other investigated model bile solutions were prepared by adding or substituting (10–20%) of the EYL or Na-TC by the synthetic bile acid conjugate (PalC).

B. Native Human Gallbladder Bile

Native human gallbladder bile was obtained from cholesterol gallstone patients at cholecystectomy. Pooled bile from several patients was cholesterol enriched by incubation with dried cholesterol or by mixing with a concentrated model bile prior to use in experiments in order to facilitate crystallization.

2. Evaluation of Cholesterol Crystal Formation and Growth 2.1 Crystal Observation Time (COT) Assay COT (also called "Nucleation time") was determined as described by Holan et al. in Gastroenterology, 77, (1979) 611–617. Aliquots from each model bile were examined daily by polarized light microscopy. COT was defined as the initial time of detection of at least three cholesterol monohydrate crystals per microscopic field at 100 fold magnification.

2.2 Crystal Growth Rate (CGR) Assay

Crystal growth was monitored spectrophotometrically using a microplate reader (SPECTRA-STL, Austria) (G. J. Somjen, et al., J. Lipid Res., 38, (1977) 1048–1052). Aliquots (50 μl) of lipid solutions were mixed and shaken vigorously with equivalent volumes of Na-taurodeoxycholate (200 mM), in microplate wells. After 60 minutes at room temperature, the microplates were shaken again and the absorbance, at 405 nm, in each well was measured. Each model was prepared in triplicate and sampled in duplicate for measurement.

The data were collected and analyzed by an IBM compatible personal computer, and the optical density (OD), averaged for triplicate preparations, was calculated. A graph describing the averaged OD changes for each solution was plotted. The slope in the steepest region of the curve was determined by a linear regression fit to at least three measurements and defined as the CGR. CGR and OD differences between day 0 and day 14 were calculated for each model.

2.3 Measurement of Crystal Mass

Chemical analyses of cholesterol were performed on each sample on the last day of the experiment (day 14), as previously described (G. J. Somjen see above). The samples were collected from the micro wells, centrifuged in an Airfuge (Beckman) at 70,000 rpm for 5 min. Separate determinations were performed on the total sample (before centrifugation) as well as on the supernatant solution. The amount of cholesterol in the precipitated pellets was calculated by subtracting the amounts in the supernatant solutions from the total. The crystalline character of the pellet was confirmed by polarized light microscopy. The crystal mass was also measured spectrophotometrically as the OD difference between day 0 and day 14 of the incubation.

3. Data Analysis

Each lipid dispersion was prepared in triplicate and duplicate aliquots were measured from all samples. Mean values of OD and standard errors were calculated. Crystal growth rates were calculated from linear regression analysis of the crystal growth curves as explained above. Comparisons between the different model solutions were performed by one way analysis of variance.

EXAMPLE XII

The effects of the bile salt fatty acid conjugate prepared in Example IV (PalC hereinafter "test compound") on cholesterol crystallization kinetics in model and human biles.

Replacement and addition experiments were performed. The following results were obtained.

A. Model Bile a. In a model bile solution (composition: Na taurocholate 150 mM, cholesterol 15 mM, egg lecithin 30 mM, total lipids 10.3 gm/dl) when 20% of the Na taurocholate was replaced by the test compound (PalC), the nucleation time was prolonged by 167%; the cholesterol crystal growth rate was reduced by 67% and the total cholesterol crystal mass after 14 days of incubation was reduced by 53%.

b. When the test compound was added to the whole model bile solution (at a concentration of 20% of bile salts), the effects were as follows:

The nucleation time was prolonged by 200%; the cholesterol crystal growth rate was reduced by 59% and the total crystal mass after 14 days of incubation was reduced by 51%.

B. Native Human Bile

When the test compound (at a concentration of 10 mM) was incubated with pooled native human gallbladder bile from patients with cholesterol gallstones, the results were as follows:

In the native human bile, from which cholesterol crystals were removed by prior ultracentrifugation for 2 hours, new cholesterol crystals were observed from day 2 of incubation (at 37° C.). Crystal numbers increased progressively reaching a peak of more than 150 crystals per microscopic field on day 14. In the same bile incubated with 10 mM of the test compound no cholesterol crystals were seen throughout the incubation period of 21 days.

EXAMPLE XIII

Nucleation studies of cholesterol crystals in model biles were performed as follows:

PalC was added to the model bile in the following proportions (moles %)

Replacing NaTC by 10%, 20% ("B", "C");

Replacing PC by 20% ("D"); and

Adding 10%, 20% of total NaTC ("E", "F")

Figure 1:
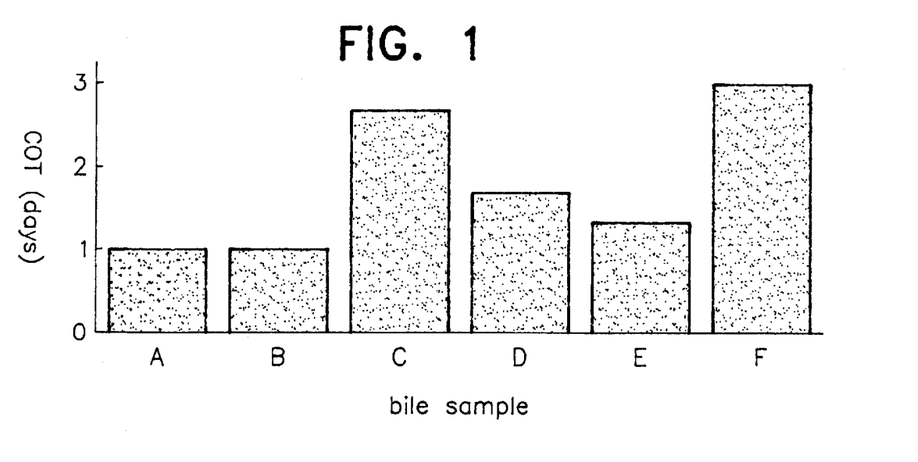
FIG. 1 shows crystal observation time. Model bile solution. Effects of palmitoyl-cholate (PalC).

The results of the Experiments of Examples XII and XIII are summarized in accompanying FIGS. 1 to 3 as follows (in all FIGS. 1 to 3 "A" represents the control model bile without PalC):

FIG. 1 illustrates the crystal observation time=nucleation time. The results are given as means of triplicates. The crystal observation time was prolonged by 167% in C and by 200% in F.

Figure 2:
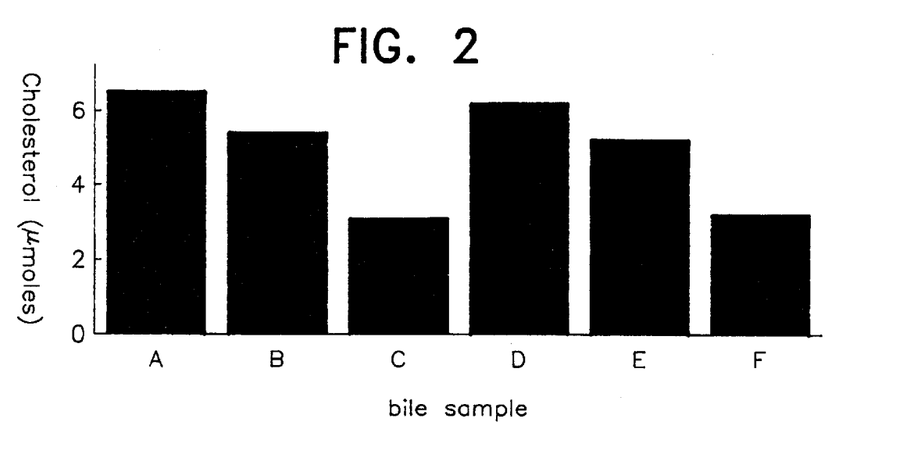
FIG. 2 shows cholesterol crystal mass. Model bile solution. Effects of PalC. A, B, C, D, E and F—as in FIG. 1.

FIG. 2 illustrates the cholesterol crystal mass. The cholesterol mass on day 14 was reduced by 17% in B and by 53% in C. It was reduced by 51% in F.

Figure 3:
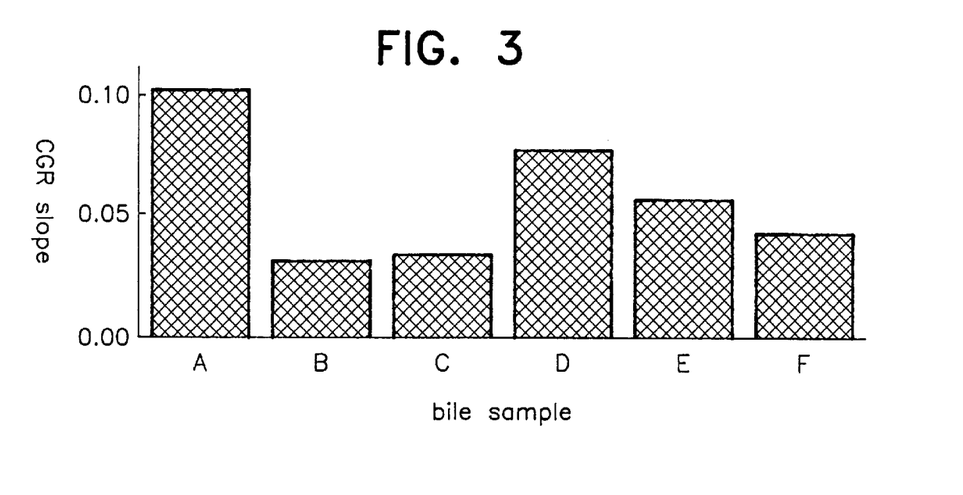
FIG. 3 shows crystal growth rate. Model bile solution. Effects of PalC. A, B, C, D, E and F—as in FIG. 1.

FIG. 3 illustrates the crystal growth rate. The crystal growth rate was reduced by 70% in B and by 59% in F.

These experimental data confirmed that conjugates of bile salts and fatty acids prevent or retard cholesterol crystallization in model and human biles.

EXAMPLE XIV

A. Animals

Male, 6–7 weeks old hamsters weighing 79–83 g were maintained in an animal house with ad libidum access to water and chow.

Test hamsters were given per os by a special syringe 10–15 mg/animal/day of PalC dissolved in 1 ml of saline. Control animals were given an equivalent volume of saline alone. Both groups behaved normally in the course of treatment. On the second day 4 hours after the application of the PalC in saline to the respective animals they were killed by an overdose of chloroform vapors. The abdomens were opened, the bile ducts were tied up, the gallbladders were excised and rinsed twice in saline. They were then placed on the top of conical plastic tubes and incised. The bile was collected at the bottom of the tubes.

2 series of animals were examined;

I. 5 control and 5 test animals each receiving 10 mg PalC/day;

II. 3 control and 9 test animals each receiving 15 mg PalC/day.

B. Biochemical Procedures

Bile samples were centrifuged (Eppendorf centrifuge) for 5 min. at 2000 rpm. Debris was discarded and the supernatant was extracted according to the Folch procedure (chloroform: methanol 2:1). After partition with water, the lipid phase was analyzed by thin layer chromatography on silica gel 60 thin layer plates (Merck). The eluent was dichloromethane:methanol:acetic acid (100:5:1, v:v:v). Samples were compared with a true standard, Reference front (Rf) about 0.2 after development with $I_2$ vapors.

C. Results

In series I 140 µl of control and 240 µl of test bile were obtained. In series II 95 µl of control and 240 µl of test bile were obtained. The control biles and the test biles of each series were separately pooled. The TLC analysis (shown in FIG. 4) of the extracted lipids demonstrated the presence of PalC in the bile of the test animals. This proves that the ingested PalC is absorbed and excreted into the bile.

Figure 4A:
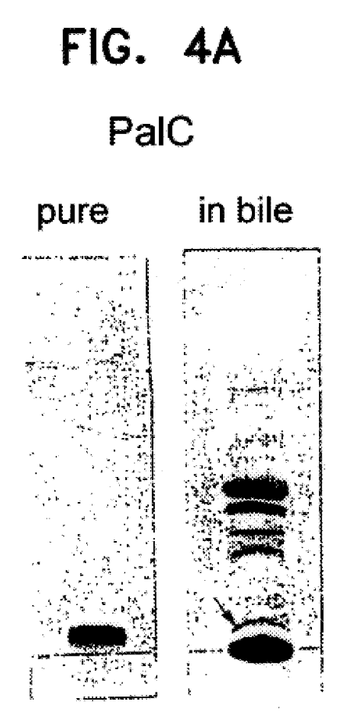
FIG. 4 shows thin layer chromatography. A—PalC standards in pure solution (left) and in hamster's bile. B—Hamster bile of control animals (left) and bile of PalC fed hamsters.
Figure 4B:
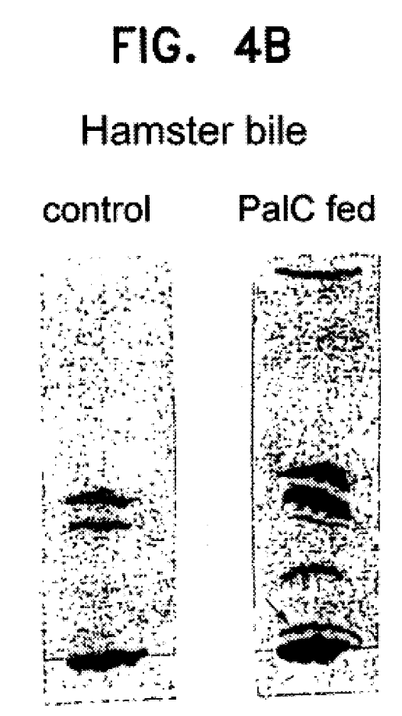

FIG. 4 illustrates TLC comparisons of the Experiments performed in Example XIV:

A. illustrates PalC standards: in pure solution (left) and in bile (right):

B. illustrates hamster biles: from control hamsters (left); and from hamsters fed with PalC (right). A PalC band is seen in this column.

FIGS. 5A, 5B, FIG. 5C and 5D illustrate the formulae of the compounds described in Examples I to X, respectively.

EXAMPLE XV

Methods

The model bile solution had the following composition:

Cholesterol 15 mM, EYL 30 ml, NaTC 150 mL. It was prepared as described in Example XI. In the test solutions 20 mole percent of NaTC was replaced by an equimolar amount of each specific fatty acid/bile acid conjugate tested. The results obtained with the conjugates of saturated fatty acids of chain length $C_{14}$, $C_{16}$, $C_{18}$ and $C_{20}$, respectively, conjugated with cholic acid at position $C_3$ are shown in FIGS. 6 and 7.

Figure 6:
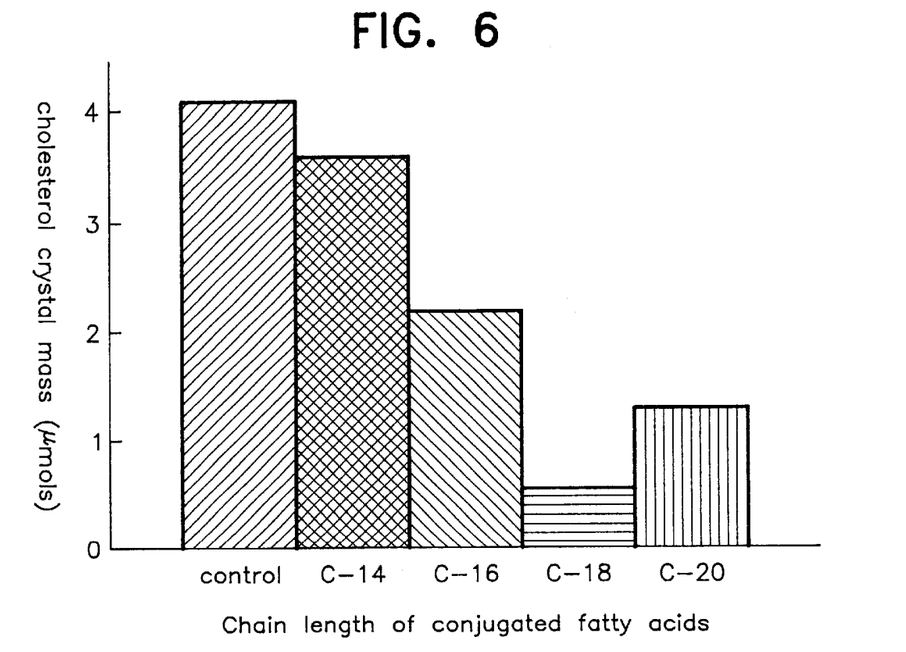
FIG. 6 shows cholesterol crystal mass. Model bile solution. Effects of myristic (C-14), palmitic (C-16), stearic (C-18) and arachidic (C-20) acids conjugated with cholic acid (at C-3). The test compounds replaced 20 mole % of the NaTC in the control solution.

FIG. 6 shows the effect of these conjugates on the cholesterol crystal mass following 14 days of incubation of the control and test solutions. All the above conjugates reduced the final crystal mass in comparison with the control solution. The $C_{18}$ conjugate reduced it to 14% of the control; the $C_{20}$ conjugate reduced it to 38%.

A conjugate of $C_{22}$ tested in a different experiment showed a similar activity to that of $C_{20}$.

Figure 7:
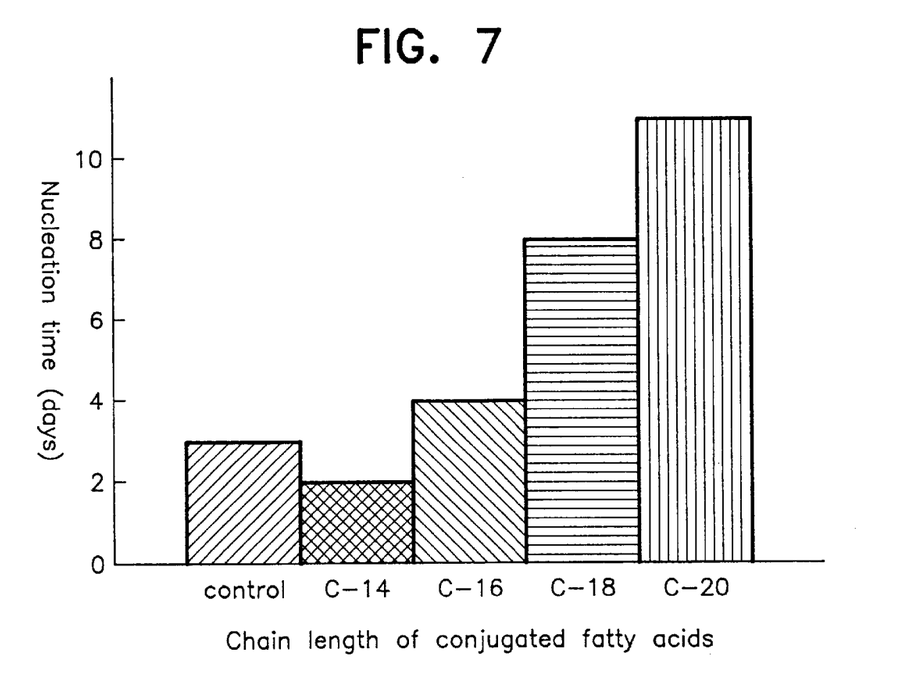
FIG. 7 shows nucleation time. Model bile solution. Effects of the compounds used in FIG. 6.

FIG. 7 shows the nucleation time (crystal observation time) of the various test solutions as compared to the control solution. Replacement of 20% of the bile salt (NaTC) by the specific conjugates resulted in a prolongation of the nucleation time with $C_{26}$, $C_{18}$ and $C_{20}$ conjugates. $C_{14}$ did not prolong the nucleation time. The $C_{20}$ conjugate prolonged the nucleation time by more than 360%.

EXAMPLE XVI

Figure 8:
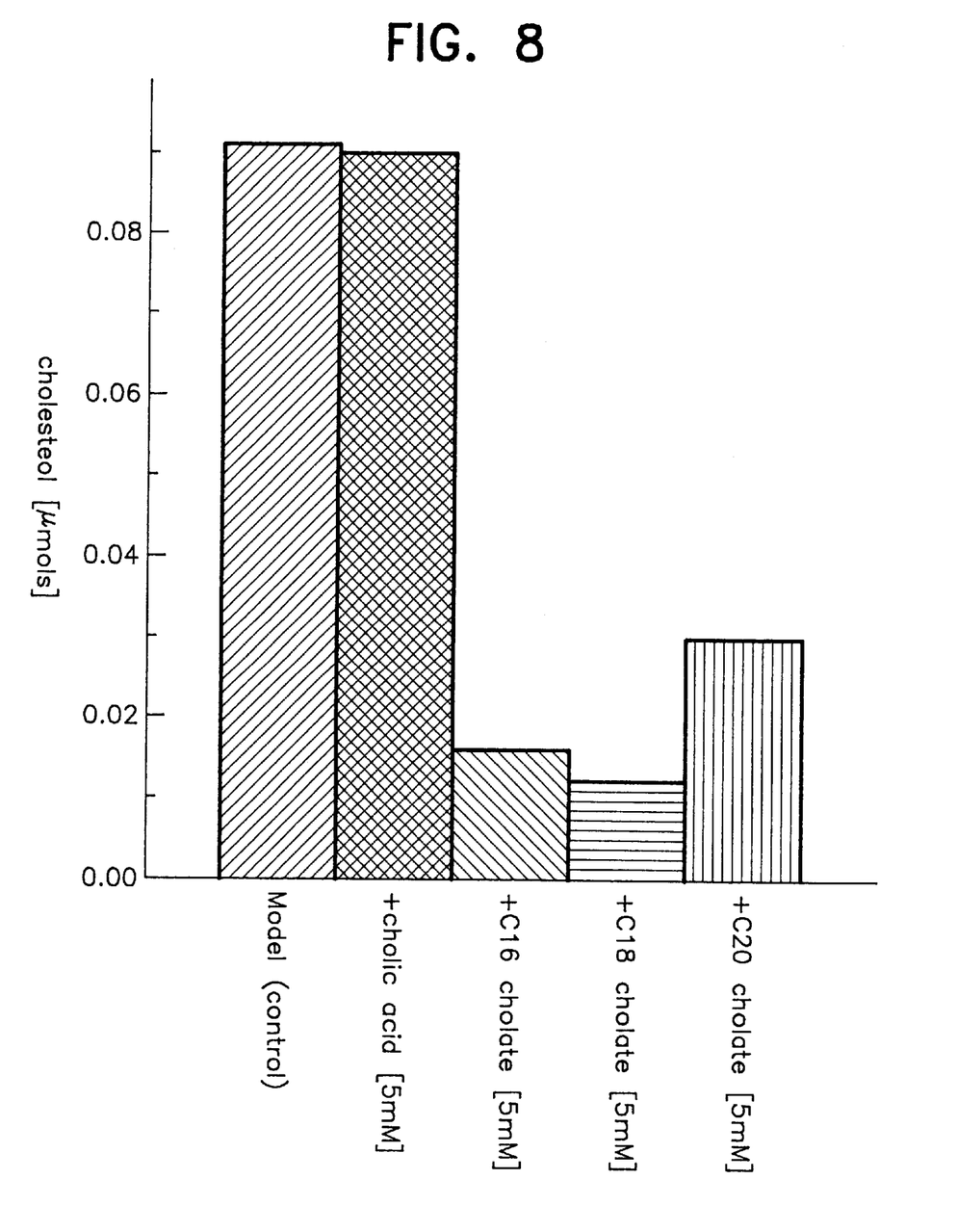
FIG. 8 shows cholesterol crystal mass of enriched human bile after 22 days of incubation. Effects of 5 mM palmitoyl (C-16) cholate, stearoyl (C-18) cholate and arachidyl (C-20) cholate added to the bile in comparison with the control bile and bile with added 5 mM cholic acid.

Pooled human gallbladder bile obtained at operations was enriched with a concentrated lipid solution to enhance cholesterol crystallization. The final concentration in bile of the added lipids was NaTC 60 mM, EYL 18.4 mM and cholesterol 9.2 mM. The enriched bile was ultracentrifuged at 50,000 rpm for 1 hour to remove cholesterol crystals and was then distributed into 5 vials. The first vial contained only enriched bile (control). To the other 4 vials the following solutions were added (at 5 mM): cholic acid, C-16 (palmitoyl) cholate, C-18 (stearoyl) cholate and C-20 (arachidyl) cholate. Following 22 days of incubation at 37° C. all biles were centrifuged in an airfuge at 70,000 rpm for 5 minutes. The sediment was removed and its cholesterol content measured chemically. The results are shown in FIG. 8, as µ moles of cholesterol in the sedimented crystal mass. It is obvious that all three bile salt/fatty acid conjugates very markedly reduced cholesterol crystallization in comparison to the control bile with or without cholic acid.

EXAMPLE XVII

A model bile solution was prepared as described in example XI, with the same lipid composition, and served as a control. In all other samples 20 mole % of the NaTC were replaced by equimolar amounts of: cholic acid, $C_6$ cholate, $C_{12}$ cholate, $C_{18}$ cholate, $C_{20}$ cholate (all these saturated fatty acids were conjugated at position $C_3$ of the cholate) and di-stearoyl ursodeoxycholate (with the stearic acid radicals conjugated in equal proportions at positions $C_3$ and $C_7$ of the bile acid).

Figure 9:
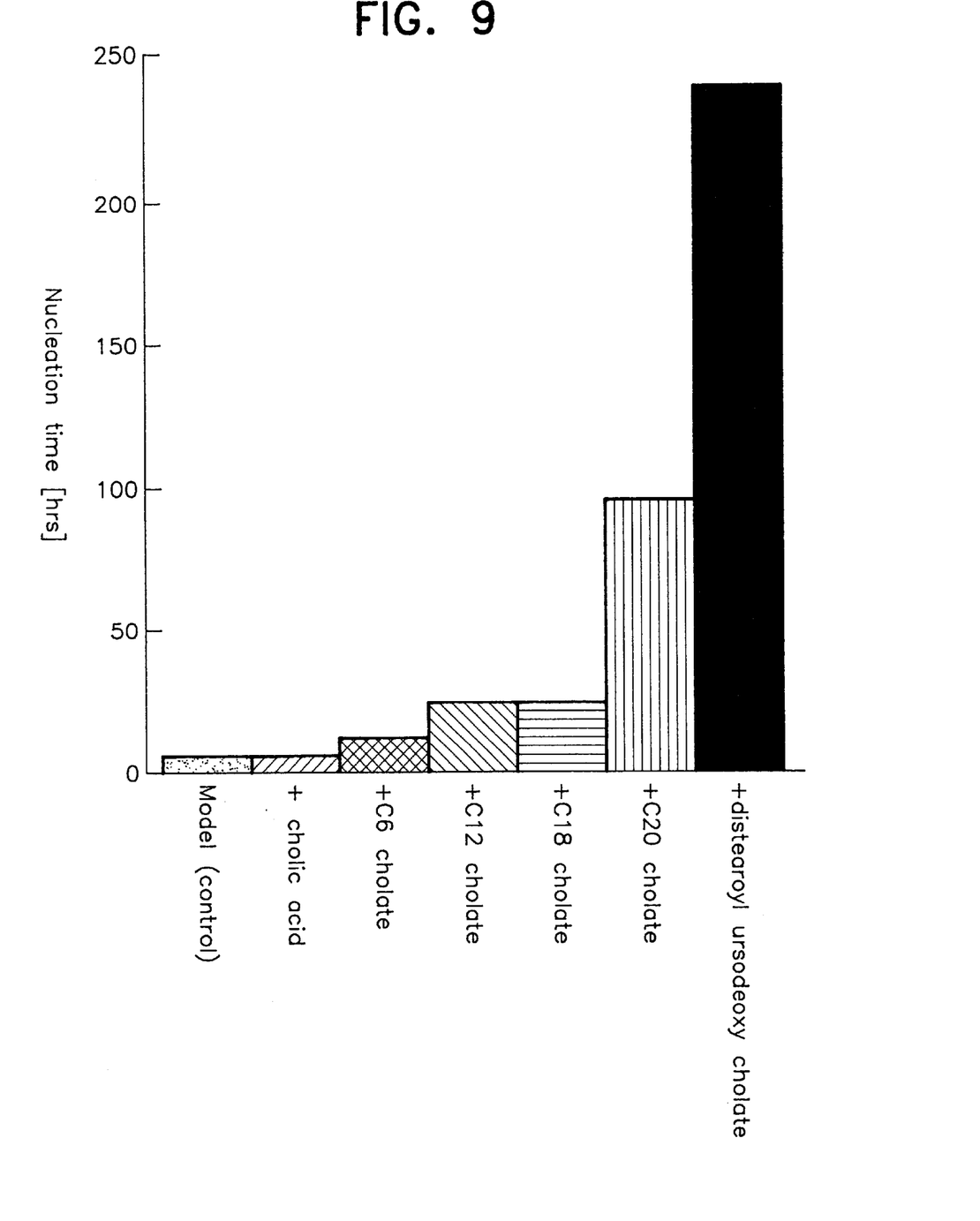
FIG. 9 shows nucleation time, model biles. Effects of replacement of 20 mole % of NaTC with equimolar amounts of caproyl (C-6) cholate, lauryl (C-12) cholate, stearoyl (C-18) cholate, arachidyl (C-20) cholate and di-stearoyl ursodeoxy-cholate in comparison with the model bile and without replacement of 20% of NaTC with cholic acid.

All samples were incubated at 37° C. in the same manner as described in example XI and the nucleation time was determined by periodic light microscopic observations. The results are shown in FIG. 9. The results proved that: 1) All conjugates (BAFAC) tested retarded cholesterol crystallization as compared to the control model bile and to equimolar amounts of cholic acid. 2) That BAFAC with longer fatty acid chains were more effective than those with shorter chains. 3) That the conjugate with 2 fatty acids (distearoyl ursodeoxycholate) was particularly effective.

EXAMPLE XVIII

Absorption and Transport of Stearoyl-Cholate (C-18 cholate)

Female hamsters weighing 80–100 gms were given a single dose of 30 mg of C-18 cholate by intragastric administration. Single animals were sacrificed at 1, 2, and 3 hours after administration. Heart blood, portal blood and gallbladder bile were sampled. Two groups of animals (A and B) were studied in parallel. Stearoyl cholate levels were measured with a HPLC instrument (Kontron Switzerland) using a UV detector at 206 nm.

Figure 10A:
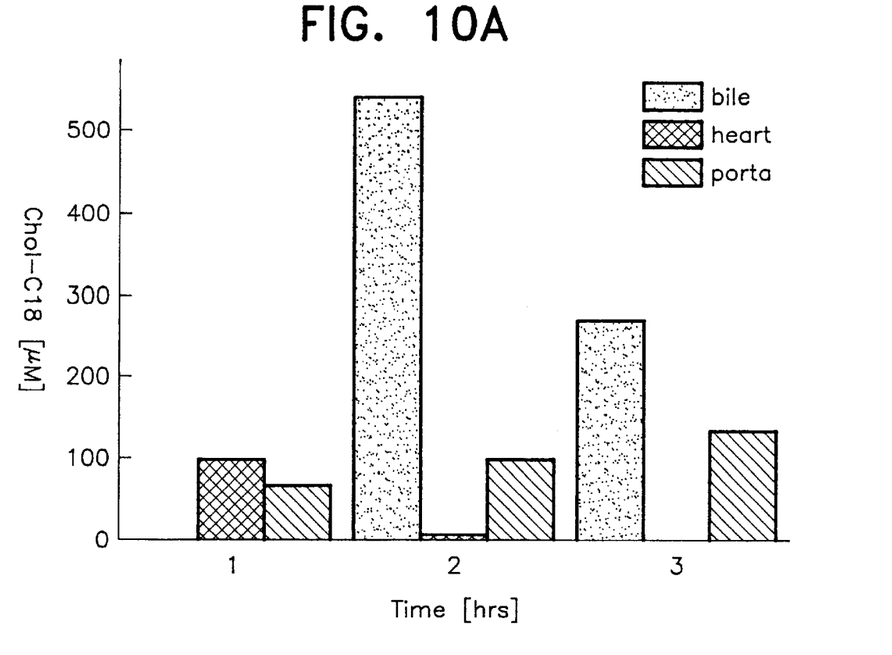
FIG. 10 shows stearoyl (C-18) cholate levels in hamsters 1, 2 and 3 hours after ingestion of 30 mg. Concentrations in heart blood, portal blood and gallbladder bile.
Figure 10B:
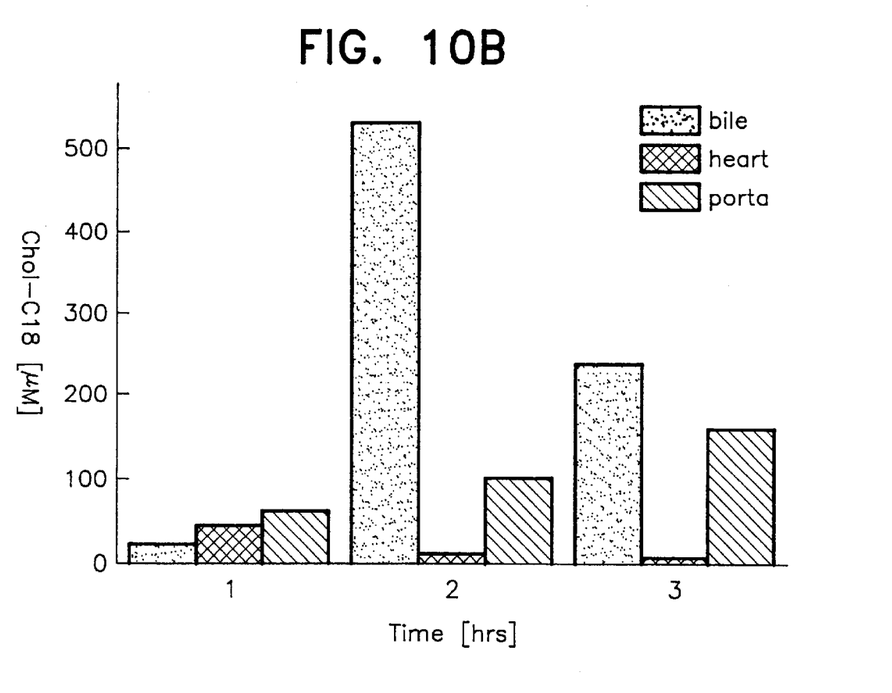

The results are shown in FIG. 10.

In group A: Heart blood levels after 1, 2 and 3 hours were 99, 7, 2 $\mu M$, while portal blood levels were 68, 99 and 133 $\mu M$, respectively. C-18 cholate levels in gallbladder bile wre 540 and 270 $\mu M$ at 2 and 3 hours, respectively. Results in group B were similar.

The data show: 1) That C-18 (stearoyl) cholate is absorbed from the intestine. 2) That it is transported both in the systemic circulation (via the lymph) and in the portal vein 3) That it is actively secreted into the bile and concentrated in it.

EXAMPLE XIX

A model bile solution was prepared in the same manner as described in Example XI. It had the same lipid composition and served as control.

In the test solutions cholic acid, stearoyl (C-18:0) cholate and oleoyl (C-18:1) cholate were added in 20 mM concentrations. All samples were incubated at 37° C. for 100 hrs. The difference in the optical density between 100 hrs. and 0 hrs. (as described in Example XI) was used to measure the total crystal mass at 100 hrs. In comparison with the control solution (100%) the crystal mass with cholic acid was 114%, with stearoyl-cholate 62% and with oleoyl-cholate 55%.

These results prove that BAFAC with a saturated as well as with an unsaturated (oleic) acid both decrease cholesterol crystallization in comparison with the control bile and with equimolar amounts of cholic acid.

What is claimed is:

1. A bile acid or bile salt fatty acid conjugate of general formula II $$W-X-G \qquad II$$

in which G is a bile acid or bile salt radical, which is optionally conjugated in position 24 with an amino acid, W stands for one or two fatty acid radicals, each having from 6 to 26 carbon atoms, and X stands for a separate nitrogen bridge (—NH—) between said bile acid or bile salt radical and each fatty acid radical.

2. A bile acid or bile salt fatty acid conjugate of general formula II $$W-X-G \qquad II$$

in which G is a bile acid or bile salt radical, which is optionally conjugated in position 24 with an amino acid, W stands for one or two fatty acid radicals, each having from 14 to 22 carbon atoms, and X stands for a separate nitrogen bridge (—NH—) between said bile acid or bile salt radical and each fatty acid radical.

3. A bile acid or bile salt fatty acid conjugate according to claim 1, wherein the bile acid is a member selected from the group consisting of cholic acid, chenodeoxycholic acid, ursodeoxycholic acid and deoxycholic acid.

4. A bile acid or bile salt fatty acid conjugate according to claim 1, wherein the amino acid in position 24 is glycine or taurine.

5. A bile acid or bile salt fatty acid conjugate according to claim 1, wherein conjugation with the fatty acid radical is at position 3 of the bile acid nucleus.

6. A bile acid or bile salt fatty acid conjugate according to claim 1, wherein conjugation with the fatty acid radical(s) is at a position selected from the 6, 7, 12 and 24 positions of the bile acid nucleus.

7. A bile acid or bile salt fatty acid conjugate according to claim 1, wherein conjugation between the fatty acid radical (s) and the bile acid is in $\alpha$ or $\beta$ configuration.

8. A bile acid or bile salt fatty acid conjugate according to claim 1, wherein the fatty acid is a saturated fatty acid selected from the group consisting of behenylic acid, arachidylic acid and stearic acid.

9. A bile acid or bile salt fatty acid conjugate according to claim 1, wherein W stands for two fatty acids which are conjugated at positions 3 and 7 of the bile acid nucleus.

10. A pharmaceutical composition enabling dissolution of cholesterol gallstones in bile, preventing formation of such gallstones and enabling prevention and/or reduction of arteriosclerosis, the composition comprising a suitable carrier and, as active ingredient, a bile acid or bile salt fatty acid conjugate of general formula II according to claim 1.

11. A pharmaceutical composition according to claim 10 in tablet, capsule, solution or emulsion form.

12. A pharmaceutical composition according to claim 10 comprising a member selected from the group consisting of a solvent, an emulgator, an enhancer of absorption, an inhibitor of cholesterol synthesis, and an inhibitor of cholesterol secretion into the bile.

13. A pharmaceutical composition according to claim 10 comprising from 0.1 to 1.5 g of the active ingredient per unit dose.

14. A method for dissolving cholesterol gallstones in bile and for preventing formation of such gallstones, which comprises administering an effective amount of a bile acid or bile salt fatty acid conjugate according to claim 1 to a subject in need of such therapy.

15. A method for dissolving cholesterol gallstones in bile or for preventing formation of such gallstones, which comprises administering an effective amount of a pharmaceutical composition according to claim 10 to a subject in need in such therapy.

16. A method for preventing or reducing arteriosclerosis which comprises administering an effective amount of a bile acid or bile salt fatty acid conjugate according to claim 1 to a subject in need of such therapy.

17. A method for preventing or reducing arteriosclerosis which comprises administering an effective amount of a pharmaceutical composition according to claim 10 to a subject in need of such therapy.

* * * * *

UNITED STATES PATENT AND TRADEMARK OFFICE
CERTIFICATE OF CORRECTION

PATENT NO. : 6,589,946 B2
DATED : July 8, 2003
INVENTOR(S) : Tuvia Gilat et al.

It is certified that error appears in the above-identified patent and that said Letters Patent is hereby corrected as shown below:

Title page,
Item [75], "Tuvia Gilat, Tel Aviv (IL)" should read -- Tuvia Gilat Tel Aviv (IL); Werner Kramer, Frankfurt Am Main (DE) --.

Signed and Sealed this

Twenty-seventh Day of April, 2004

JON W. DUDAS
*Acting Director of the United States Patent and Trademark Office*